US00PP16422P3

(12) United States Plant Patent
Cornelis

(10) Patent No.: US PP16,422 P3
(45) Date of Patent: Apr. 11, 2006

(54) ***SPATHIPHYLLUM* PLANT NAMED 'MARA'**

(50) Latin Name: *Spathiphyllum Schott.*
Varietal Denomination: Mara

(76) Inventor: Daniel Cornelis, Oude Gaverweg 2, B-9820 Melsen-Merelbeke (BE)

( * ) Notice: Subject to any disclaimer, the term of this patent is extended or adjusted under 35 U.S.C. 154(b) by 339 days.

(21) Appl. No.: 10/916,838

(22) Filed: Aug. 12, 2004

(65) Prior Publication Data

US 2005/0039239 P1 Feb. 17, 2005

(51) Int. Cl.
*A01H 5/00* (2006.01)

(52) U.S. Cl. ..... Plt./364

(58) Field of Classification Search ..... Plt./364
See application file for complete search history.

*Primary Examiner*—Anne Marie Grunberg
(74) *Attorney, Agent, or Firm*—Mark P. Bourgeois

(57) ABSTRACT

A new cultivar of *Spathiphyllum* plant named 'Mara' that is characterized by upright strong leaves with undulate margins, minimal shoots and consistent flowering.

1 Drawing Sheet

Botanical classification: *Spathiphyllum Schott.*
Variety denomination: 'Mara'.

BACKGROUND OF THE INVENTION

The present invention relates to a new and distinct cultivar of *Spathiphyllum* plant botanically known as *Spathiphyllum Schott.* and hereinafter referred to by the cultivar name 'Mara'.

'Mara' is a hybrid that originated from the induced hybridization of the female or seed parent an unidentified *Spathiphyllum Schott.* (not patented) and the male or pollen parent an unidentified *Spathiphyllum Schott.* (not patented). The cultivar 'Mara' was selected by the inventor in 2000 as a single plant within the progeny of the stated cross in Melsen-Merelbeke, Belgium.

Asexual reproduction by tissue culture of the new cultivar 'Mara' was first performed in 2001 in Melsen-Merelbeke, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Spathiphyllum* cultivar 'Mara'.

1. *Spathiphyllum* 'Mara' exhibits upright strong leaves with undulate margins.
2. *Spathiphyllum* 'Mara' exhibits minimal shoots.
3. *Spathiphyllum* 'Mara' exhibits consistent flowering.

The closest comparison cultivar is *Spathiphyllum* 'Alpha CD'. The new cultivar 'Mara' is distinguishable from 'Alpha CD' by the following characteristics:

1. 'Mara' flowers earlier than 'Alpha CD'.
2. 'Mara' has a larger over all size than 'Alpha CD'.
3. 'Mara' has lighter green leaves than those of 'Alpha CD'.
4. 'Mara' has a larger spathe than 'Alpha CD'.
5. 'Mara' has a shorter and thicker spadix than 'Alpha CD'.

The new cultivar 'Mara' is distinguishable from the unidentified male parent *Spathiphyllum* in having a more spreading habit and leaves that are less wavy. The new cultivar 'Mara' is distinguishable from the unidentified female parent *Spathiphyllum* in having a smaller size and leaves that are less wavy.

BRIEF DESCRIPTION OF THE DRAWING

The accompanying photograph illustrates the distinguishing traits of *Spathiphyllum* 'Mara'. The plant in the photograph shows an overall view of a 27 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Spathiphyllum* cultivar named 'Mara'. Data was collected in De Kwakel, The Netherlands from 27 month old greenhouse grown plants in 30 cm containers. The time of year was Summer and the average temperature was 21 degrees Centigrade during the day and 18 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Mara' has not been tested under all possible conditions and phenotypic differences may be observed with variations in environmental, climatic, and cultural conditions, however, without any variance in genotype.

Botanical classification: *Spathiphyllum Schott.* 'Mara'.
Use: Ornamental.
Parentage: 'Mara' is a hybrid plant that resulted from the induced hybridization of the following parent plants:
*Female parent.*—An unidentified *Spathiphyllum Schott.*
*Male parent.*—An unidentified *Spathiphyllum Schott.*
Vigor: Moderate to high.

Growth rate: Moderate to high.
Growth habit: Freely clumping, outwardly arching, bushy and dense foliage.
Plant shape: Upright, somewhat outwardly spreading.
Suitable container size: 21 cm diameter container.
Height: Average 73 cm to top of leaf plane, 103 cm to top of inflorescences.
Width: Average 108 cm. in width.
Hardiness: USDA Zone 10.
Propagation: Tissue culture.
Time to initiate roots (summer and winter): Approximately 8 days to produce roots on an initial cutting.
Time to produce a rooted cutting or liner (summer and winter): Approximately 16 days.
Root system: Fine and fibrous.
Stem: No stems, Leaves grow directly from base, Average 15 clumps, clump color 143A.
Foliage:
*Texture.*—Smooth, slightly leathery.
*Leaf arrangement.*—Alternate.
*Compound or single.*—Single.
*Leaf shape.*—Elliptic.
*Leaf apex.*—Apiculate.
*Leaf base.*—Attenuate.
*Leaf length.*—Average 33.2 cm in length.
*Leaf width.*—14.8 cm in width.
*Quantity of leaves per clump.*—Average 10.
*Pubescence.*—Absent.
*Leaf margin.*—Entire, slightly wavy.
*Vein pattern.*—Pinnate.
*Young leaf color* (*upper surface*).—Between 141A and 143A.
*Young leaf color* (*lower surface*).—146A/147B.
*Mature leaf color* (*upper surface*).—137A.
*Mature leaf color* (*lower surface*).—137A.
*Vein color* (*lower surface*).—144A/B.
*Vein color* (*upper surface*).—137B.
*Leaf attachment.*—Petiolate.
*Petiole dimensions.*—Average 38 cm in length excluding geniculum, 5.5 mm in diameter below geniculum to 1 cm in diameter above clump.
*Petiole aspect.*—Round.
*Petiole color.*—137A.
*Geniculum dimensions.*—Average 3.9 cm in length and 6 mm in diameter.
*Geniculum aspect.*—Rounded.
*Geniculum color.*—143A.
*Petiole sheath dimensions.*—Average 22.3 cm in length and 7 mm in diameter.
*Petiole sheath color.*—143A.
*Durability of foliage to stress.*—High.
Inflorescence:
*Inflorescence arrangement.*—Spathes with spadices held above the foliage on erect peduncles arising from the petiole sheath.
*Flowering habit.*—Continuous.
*Quantity of spathes per plant.*—7.
*Natural flowering season.*—Autumn to winter.
*Time to flower or response time.*—6 months.
*Fragrance.*—Moderate, sweet.
*Self-cleaning or persistent.*—Persistent.
*Flower longevity.*—Lasts approximately 3 weeks on plant.
*Spathe aspect.*—Concave, cupped.
*Spathe dimensions.*—Average 17.8 cm in length, 9.6 cm in width and 6.8 cm in depth.
*Spathe texture.*—Glabrous, slightly leathery.
*Spathe shape.*—Broad elliptic.
*Spathe margin.*—Entire.
*Spathe apex.*—Apiculate, twisted.
*Spathe base.*—Cuneate.
*Spathe color when opening* (*front side*).—155C.
*Spathe color when opening* (*back side*).—155C.
*Spathe color when fully opened* (*front side*).—155C.
*Spathe color when fully opened* (*back side*).—155C with a vein 143A/B.
*Spathe color fading to.*—Not fading.
*Spadix shape.*—Columnar, arising from top of peduncle.
*Spadix tip.*—Obtuse.
*Spadix base.*—Obtuse.
*Spadix dimensions.*—Average 7.1 cm in length and 1.7 mm in diameter.
*Spadix color when opening.*—158A.
*Spadix color when fully opened.*—158A.
*Quantity of flowers per spadix.*—Average 250.
*Spadix flower arrangement.*—Bisexual, rounded.
*Spadix flower dimensions.*—4 mm in diameter and 3 mm in depth.
Reproductive organs:
*Anther color.*—158D.
*Amount of pollen.*—Moderate.
*Pollen color.*—158C/D.
*Stigma color.*—158C.
*Ovary color.*—158C.
Peduncle:
*Peduncle dimensions.*—Average 75.8 cm in length and 5.5 mm. in diameter.
*Peduncle angle.*—10 degrees.
*Peduncle color.*—137A.
*Peduncle strength.*—Strong.
Seed: Seed production has not been observed.
Disease and insect resistance: Plants of the new *Spathiphyllum* have not been observed for disease or insect resistance.

It is claimed:

1. A new and distinct variety of *Spathiphyllum* plant named 'Mara' as described and illustrated.

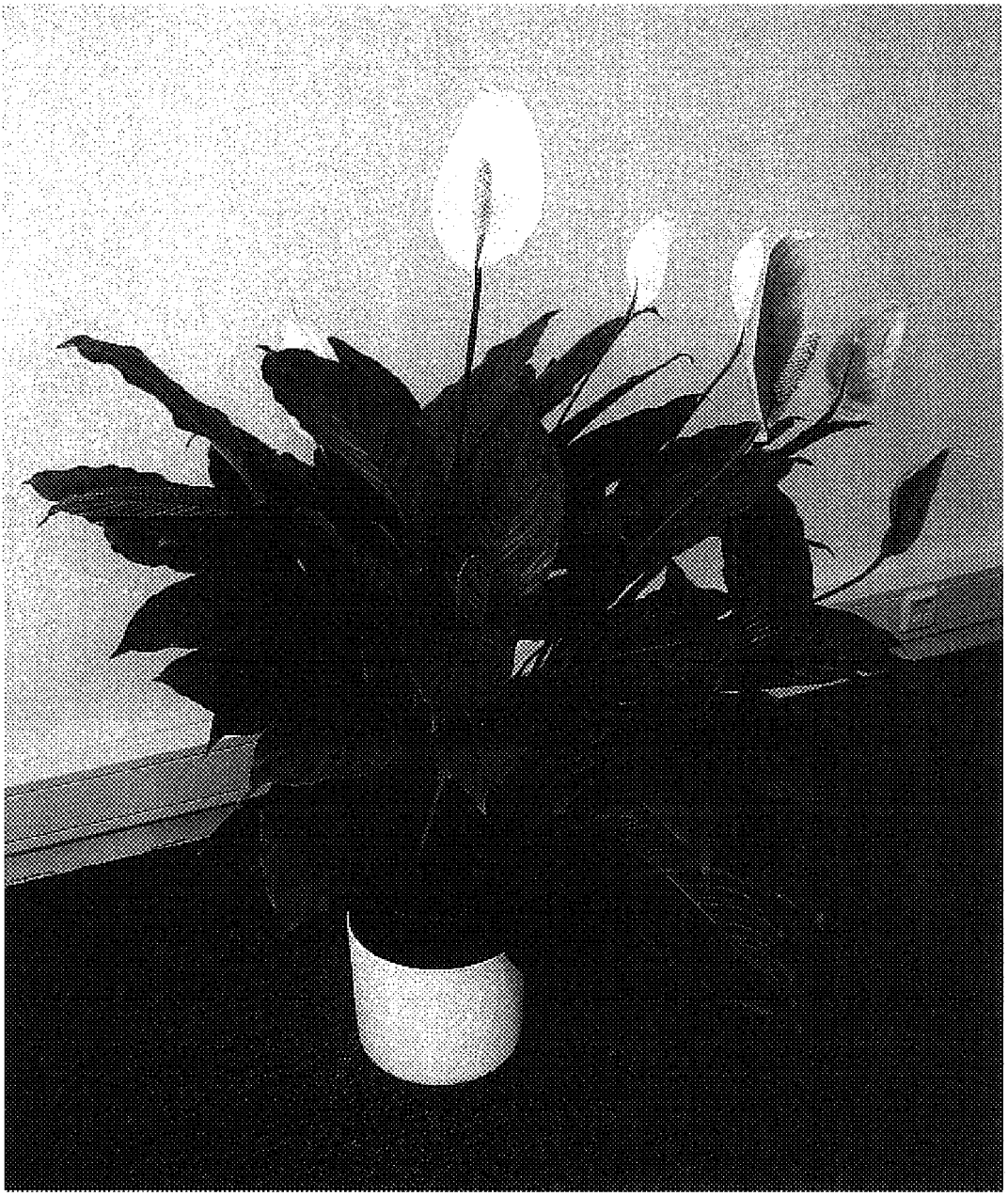

* * * * *